US006614531B2

United States Patent
Sato et al.

(10) Patent No.: US 6,614,531 B2
(45) Date of Patent: Sep. 2, 2003

(54) APPARATUS FOR DETECTING IMPURITIES IN MATERIAL AND DETECTING METHOD THEREFOR

(75) Inventors: Kiyomi Sato, Tokyo (JP); Tsuyoshi Futamura, Tokyo (JP); Shinzo Kida, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 10/005,076

(22) Filed: Dec. 7, 2001

(65) Prior Publication Data

US 2002/0039185 A1 Apr. 4, 2002

Related U.S. Application Data

(63) Continuation of application No. PCT/JP00/03669, filed on Jun. 6, 2000.

(51) Int. Cl.[7] .............................................. G01N 21/84
(52) U.S. Cl. ................................. 356/429; 356/237.1
(58) Field of Search ............................. 356/429, 237.1

(56) References Cited

U.S. PATENT DOCUMENTS 4,776,702 A * 10/1988 Yamaba ..................... 250/226
5,134,278 A * 7/1992 Nelen ....................... 250/223 B
5,305,893 A 4/1994 Hereford
5,462,176 A 10/1995 Hereford et al.
5,729,473 A * 3/1998 Blanc et al. ................ 209/580
5,914,247 A * 6/1999 Casey et al. ............... 356/317

FOREIGN PATENT DOCUMENTS

| JP | 62-144034 A | 6/1987 |
| JP | 62-170963 A | 7/1987 |
| JP | 62-188945 A | 8/1987 |
| JP | 4-242157 A | 8/1992 |
| JP | 7-336608 A | 12/1995 |

* cited by examiner

Primary Examiner—Frank G. Font
Assistant Examiner—Roy M Punnoose
(74) Attorney, Agent, or Firm—Birch, Stewart, Kolasch & Birch, LLP

(57) ABSTRACT

In an apparatus and a method for detecting impurities in a material, infrared rays or a plurality of specific wavelength components of the infrared rays are applied to a material (T) on a conveyor (2), the respective reflection intensities of the specific wavelength components reflected by the material (T) are measured, the measured reflection intensities and the reflection intensities of specific wavelength components inherent to the material (T) are compared, and impurities in the material (T) are detected according to the result of the comparison.

13 Claims, 7 Drawing Sheets

APPARATUS FOR DETECTING IMPURITIES IN MATERIAL AND DETECTING METHOD THEREFOR

This application is a Continuation of copending PCT International Application No. PCT/JP00/03669 filed on Jun. 6, 2000, which was not published in English and which designated the United States, and on which priority is claimed under 35 U.S.C. §120, the entire contents of which are hereby incorporated by reference.

TECHNICAL FIELD

The present invention relates to an impurity detecting apparatus for efficiently detecting various foreign substances or impurities in a material and a detecting method therefore.

BACKGROUND ART

Tobacco leaves, a harvest, are packed in various forms as they are carried into tobacco material plants or cigarette manufacturing plants. After they are unpacked in these plants, the tobacco leaves are separated according to their varieties or mixed with other varieties. In this state, they are transported as the material for cigarettes to the next stage.

In some cases, materials in a transportation process may be mixed with some foreign substances, such as wrappers or strings used to pack tobacco leaves or some pieces of moisture-proof paper used to line packages. These foreign substances or impurities must be removed in the material transportation process. To attain this, the impurities should be detected during the material transportation. If the impurities include any plastic materials that produce poisonous gases as they burn, in particular, they must be securely detected and removed.

Conventionally, a detecting apparatus with a video camera is used to detect impurities. According to this detecting apparatus, the video camera shoots the material being transported, and a decision circuit of the apparatus then detects impurities in the material according to image data obtained by the shooting. More specifically, the decision circuit detects the impurities in the materials in accordance with differences in color between tobacco leaves and the impurities.

The detecting apparatus described above can be effectively used only in the case where the colors of the impurities to be detected differ substantially from those of the tobacco leaves. If the impurities have the same or similar colors as the tobacco leaves, therefore, they cannot be detected practically.

If the tobacco leaves are of a same variety, moreover, they have their respective colors, which substantially vary depending on the quality of the leaves. In the case where the material include tobacco leaves of different varieties, in particular, therefore, it is very hard to detect impurities in them.

DISCLOSURE OF THE INVENTION

The object of the present invention is to provide a detecting apparatus and a method capable of accurately detecting impurities in a material without regard to differences in color between the material consisting of tobacco leaves and a plurality of kinds of impurities.

A detecting apparatus of the present invention comprises an illuminating device for applying detection light to a material when the material is transported, a light receiving device for receiving the detection light reflected by the material, a plurality of light receiving devices being capable of outputting respective reflection intensities of a plurality of specific wavelength components of the detection light, where the specific wavelength components have different reflection intensities, respectively, between the material and impurities, and decision circuit for comparing the respective reference reflection intensities of the specific wavelength components inherent in the material and the reflection intensities delivered from the plurality of light receiving devices and detecting the impurities in the material according to the result of the comparison.

The principle of detection of impurities according to the present invention is based on definite differences in reflection intensity for the specific wavelength components of the detection light between the material and the impurities, obtained when the detection light is applied to the material and the impurities and the reflectance or reflection intensity of the detection light reflected by the material and the impurities is measured.

If the material and the impurities have the same color, therefore, the impurities in the material can be detected by comparing the respective reference reflection intensities of the specification wavelength components inherent in the material and the respective reflection intensities of the measured specific wavelength components, with respect to the specific wavelength components of the detection light.

Infrared rays or laser beams may be used as the detection light.

In the case where the illuminating device of the detecting apparatus includes a source of generation for generating infrared rays, each light receiving device includes extracting means for extracting the specific wavelength components of the infrared rays reflected by the material, and outputs the respective reflection intensities of the extracted specific wavelength components.

More specifically, the illuminating device may further include a rotatable polygon mirror, the polygon mirror being capable of reflecting the infrared rays from the source of generation onto the material on the conveyor and scanning the material on the conveyor with the reflected infrared rays in the transverse direction of the conveyor. Preferably, the polygon mirror transmits the reflected infrared rays to the light receiving device. In this case, a compact detecting apparatus can be provided.

It is desirable that the light receiving device outputs reflection intensities of at least three specific wavelength components of the detection light.

The light receiving device may include an infrared camera having a range that covers an entire transportation width of the material. In this case, the infrared camera includes dividing means for dividing received reflected infrared rays into a plurality of separate beams of infrared rays, a plurality of band-pass filters for extracting specific wavelength components from the separate beams, respectively, said specific wavelength components differing from each other and a plurality of infrared line scanners for receiving the specific wavelength components extracted by the band-pass filters and outputting reflection intensity distributions of the received specific wavelength components, respectively.

The illuminating device of the detecting apparatus can apply only the specific wavelength components of the detection light to the material. For example, the illuminating device includes a source of generation for generating infrared rays as the detection light and extracting means for extracting the specific wavelength components from the source of generation, and the illuminating device applies only the extracted specific wavelength components to the material on the conveyor.

In the case where infrared rays are used as the detection light, the infrared rays heat the material. In the case where only the specific wavelength components of the infrared rays are applied to the material, however, the material receives little thermal energy, so that the material can be prevented from overheating. In consequence, there is no possibility of the material drying excessively during the detection of the impurities, so that the quality of the material can be maintained.

Preferably, the illuminating device further includes cooling means for cooling the source of generation of the infrared rays. In this case, heat release from the illuminating device can be reduced.

The detecting method of the present invention is carried out using the detecting apparatus described above.

BEST MODE FOR CARRYING OUT THE INVENTION

Figure 1:
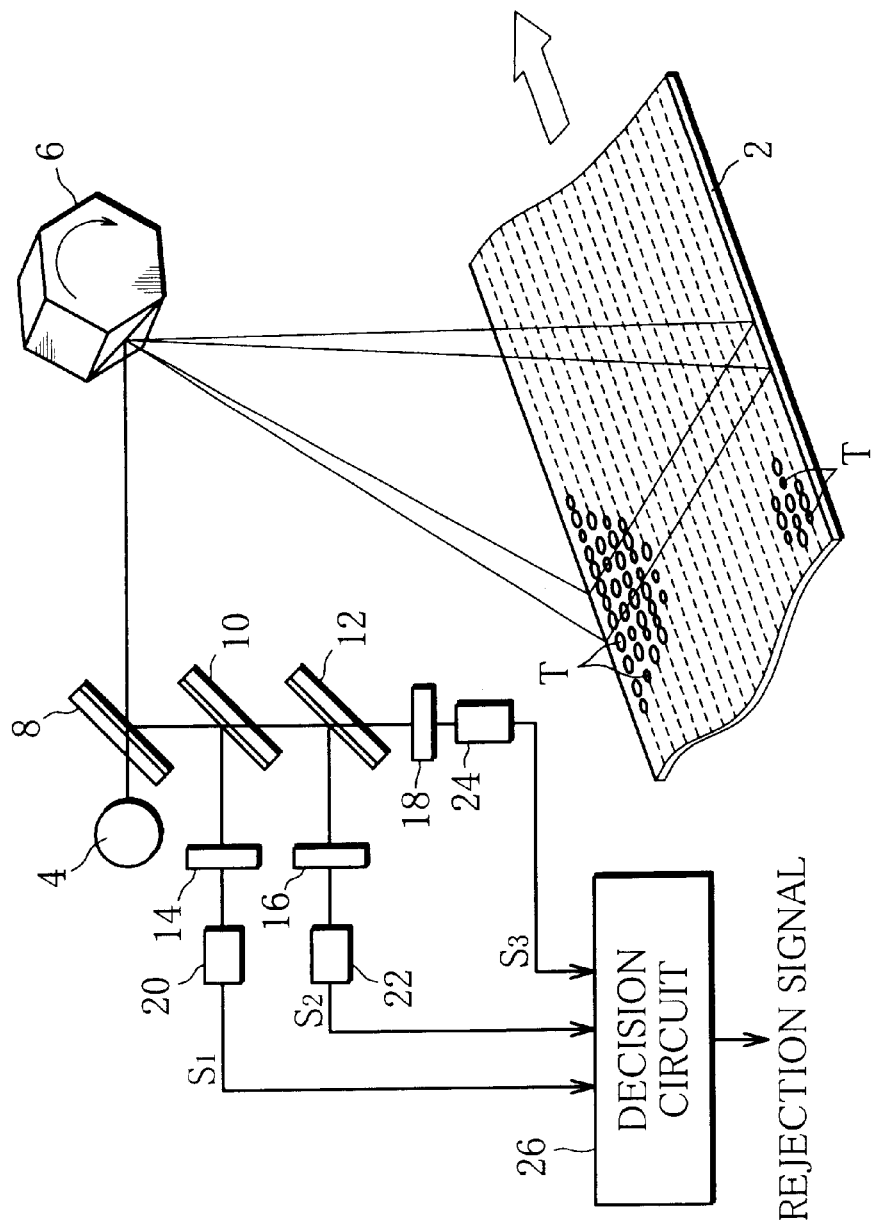
FIG. 1 is a schematic view showing a detecting apparatus of a first embodiment for executing an impurity detecting method.

Referring to FIG. 1, a detecting apparatus of a first embodiment comprises a conveyor 2, and the conveyor 2 transfers a material T in the direction of the arrow in FIG. 1. The material T is a mixture of tobacco leaves of a plurality of qualities, and is distributed thin on the conveyor 2. For example, the material T includes tobacco leaves of four varieties, domestic variety, barley variety, oriental variety, and yellow variety.

The detecting apparatus further comprises a light source 4, such as an infrared lamp, and emits infrared rays. A polygon mirror 6 is located over the conveyor 2 and rotates in one direction. The rotation of the polygon mirror 6 deflects the infrared rays emitted from the light source 4 toward the material T on the conveyor 2, and the whole transverse area of the conveyor 2 is scanned with the deflected infrared rays. On the other hand, the reflected infrared rays from the material T are transmitted to the side of the light source 4 via the polygon mirror 6 also.

A half-mirror 8 is located between the light source 4 and the polygon mirror 6. Although the half-mirror 8 transmits the infrared rays emitted from the light source 4 toward the polygon mirror 6, it deflects the reflected infrared rays from the polygon mirror 6 in a given direction.

Dichroic mirrors 10 and 12 are arranged successively from the side of the half-mirror 8 in a path of deflection of the reflected infrared rays. The dichroic mirror 10 deflects some of the reflected infrared rays as first reflected infrared rays, and transmits the remainder toward the dichroic mirror 12. The dichroic mirror 12 deflects some of the reflected infrared rays transmitted through the dichroic mirror 10 as second reflected infrared rays, and transmits the remainder as third reflected infrared rays.

After the first to third reflected infrared rays are transmitted through first to third band-pass filters 14, 16 and 18, they are supplied to first to third infrared detectors 20, 22 and 24, respectively. The first to third band-pass filters 14, 16 and 18 transmit only components of specific wavelengths out of the reflected infrared rays, and supply them to their corresponding infrared detectors. The first to third infrared detectors 20 to 24 convert their corresponding wavelength component levels, that is, reflection intensities, into electrical signals, and supply these electrical signals as first to third detection signals $S_1$, $S_2$, and $S_3$ to a decision circuit 26.

The first to third band-pass filters 14, 16 and 18 extract first to third wavelength components, respectively, from the reflected infrared rays. The respective wavelengths of these wavelength components are selected so that they effectively serve for the discrimination between the material T and impurities. More specifically, the wavelengths of the first to third reflection components are 1,200 nm, 1,700 nm, and 1,940 nm, respectively.

The following is a description of the reason why the aforesaid first to third reflection components are selected.

Figure 2:
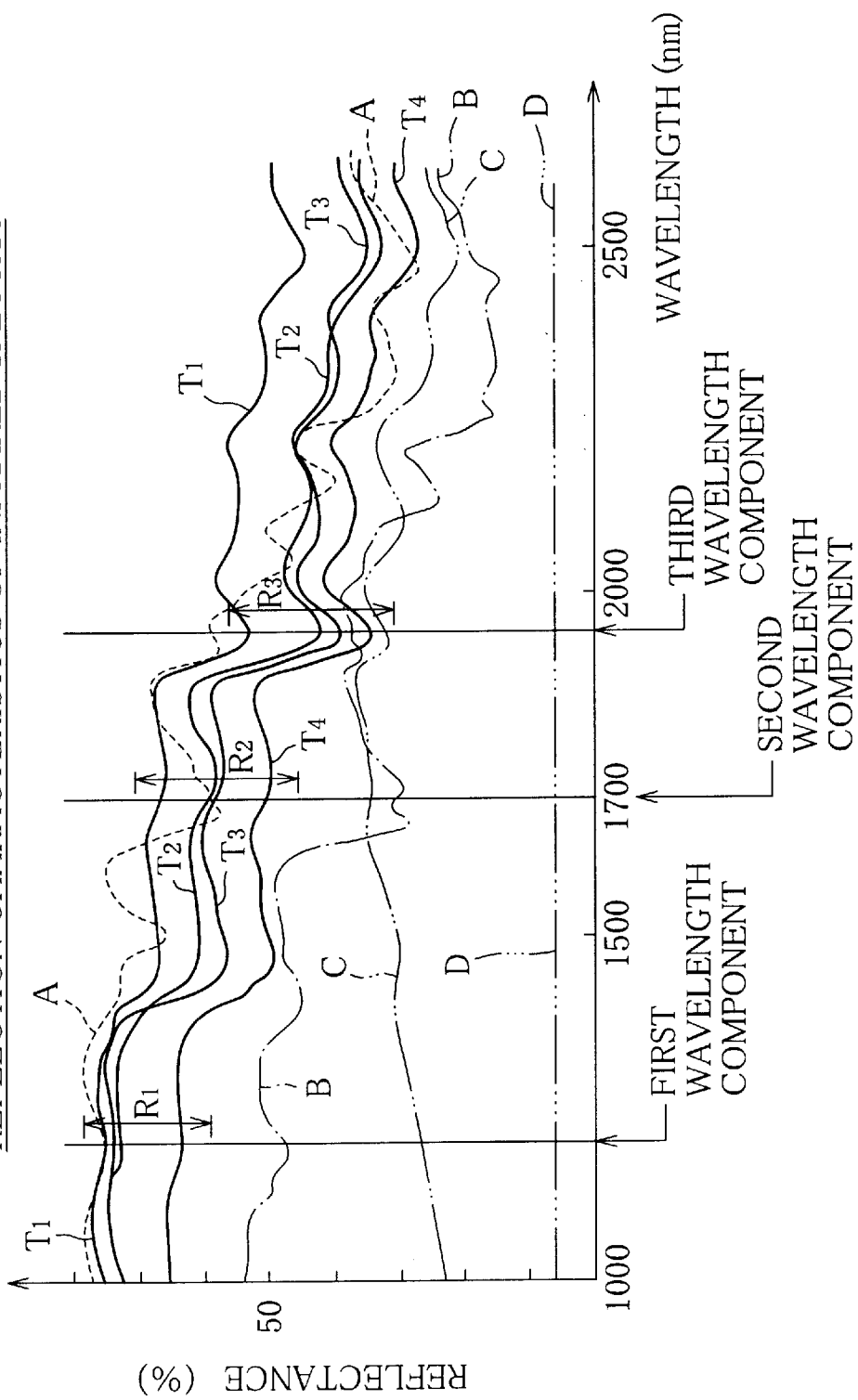
FIG. 2 is a graph showing reflection characteristics of infrared spectra obtained from a material and various impurities.

In FIG. 2, full lines $T_1$, $T_2$, $T_3$, and $T_4$ represent the reflection characteristics of infrared spectra reflected by the domestic, barley, oriental, and yellow varieties, respectively.

In FIG. 2, on the other hand, broken line A, dashed line B, and two-dot chain line C represent the reflection characteristics of infrared spectra reflected by various impurities, individually. More specifically, the reflection characteristics A, B and C are obtained from a plastic material, such as a wrapper or string, used to pack tobacco leaves, urethane foam that forms a package, and moisture-proof paper used to line the package, respectively. Further, a reflection characteristic D indicated by three-dot chain line in FIG. 2 is obtained from black synthetic rubber that forms a belt of the conveyor 2.

As seen from FIG. 2, the reflection characteristics $T_1$, $T_2$, $T_3$, and $T_4$ have some differences that are attributable to differences in color of the tobacco leaves. However, the reflection characteristics $T_1$, $T_2$, $T_3$, and $T_4$ have similar tendencies.

As far as the first wavelength component (1,200 nm) is concerned, it is hard to discriminate the reflection characteristic A (broken line) of the plastic material from the reflection characteristics $T_1$ to $T_3$ of the tobacco leaves. As far as the third wavelength component is concerned, however, the reflection characteristic A can be clearly discriminated from any of the reflection characteristics $T_1$, $T_2$, $T_3$, and $T_4$ of the tobacco leaves.

With respect to the third wavelength component, on the other hand, the reflection characteristics B and C of urethane foam and moisture-proof paper cannot be clearly discriminated from the individual reflection characteristics $T_1$, $T_2$, $T_3$, and $T_4$ of the tobacco leaves. With respect to the first or second wavelength component, however, they can be discriminated from any of the reflection characteristics $T_1$, $T_2$, $T_3$, and $T_4$.

Thus, FIG. 2 indicates that the impurities in the material T can be detected if a region that covers the reflectances of the reflection characteristics ($T_1$, $T_2$, $T_3$, and $T_4$) of the material T for the first to third wavelength components, that is, reflection intensity regions $R_1$, $R_2$ and $R_3$, and the reflection intensities of the first to third wavelength components are compared.

Figure 3:
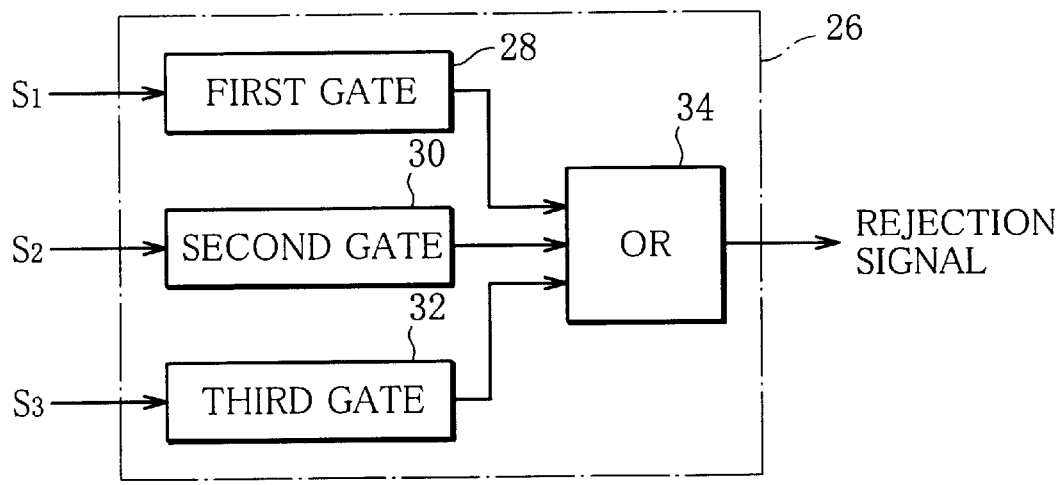
FIG. 3 is a block diagram specifically showing a decision circuit of FIG. 1.

As shown in FIG. 3, therefore, the decision circuit 26 is provided with first to third gate circuits 28, 30 and 32. These gate circuits 28, 30 and 32 receive the aforesaid first to third detection signals $S_1$, $S_2$, and $S_3$, respectively, at their input terminals, and the output terminals of these gate circuits are connected individually to an OR circuit 34. The first to third gate circuits 28, 30 and 32 have their respective upper and lower limit values, and these upper and lower limit values represent threshold values that correspond to the opposite end levels of their corresponding reflection intensity regions $R_1$, $R_2$ and $R_3$.

If a detection signal S that is supplied to one gate circuit is deviated from a tolerance that is defined between the upper and lower limit values of the gate circuit, the gate circuit delivers an on-signal to the OR circuit 34, whereupon the OR circuit 34 outputs a rejection signal.

In the case where the OR circuit 34 outputs a rejection signal in response to an on-signal from the first gate circuit 28, as is already evident from the foregoing description, the rejection signal indicates the presence of impurities with the reflection characteristic B or C in the material T. Likewise, in the case where the OR circuit 34 outputs a rejection signal in response to an on-signal from the second gate circuit 30 or the third gate circuit 32, the rejection signal indicates the presence of impurities with the reflection characteristic A, B, or C in the material T.

The rejection signal from the OR circuit 34 is supplied to a rejecting device (not shown). The rejecting device is located in a path of transfer of the material T on the lower-stream side of the polygon mirror 6. When reached by the material T containing the impurities, the rejecting device removes the material T that covers the whole transverse area of the conveyor 2, along with the detected impurities, from the path of transfer.

The aforesaid decision circuit 26 can not only detects the impurities in the material T, but also specify the position of the detected impurities. More specifically, when the impurities are detected by means of the decision circuit 26, the infrared scanning position on the conveyor 2, that is, the position of the impurities, is determined in accordance with the angle of deflection of the infrared rays by means of the aforesaid polygon mirror 6. In this case, the rejecting device can reject the material T around the impurities, along with the impurities, with respect to the transverse direction of the conveyor 2, so that the amount of reflection of the material T can be reduced.

In the case of the detecting apparatus of the foregoing first embodiment, the same path is used for the transmission of the infrared rays to the material T and the transmission of the reflected infrared rays from the material T, so that the provided detecting apparatus is compact.

Figure 4:
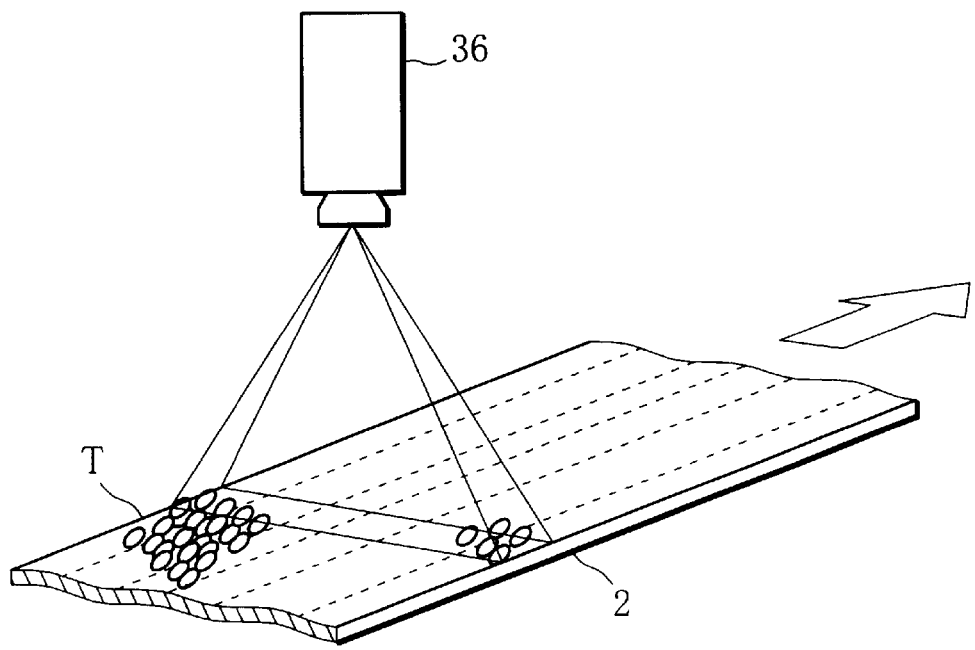
FIG. 4 is a view showing a configuration of an infrared camera used in a detecting apparatus of a second embodiment.
Figure 5:
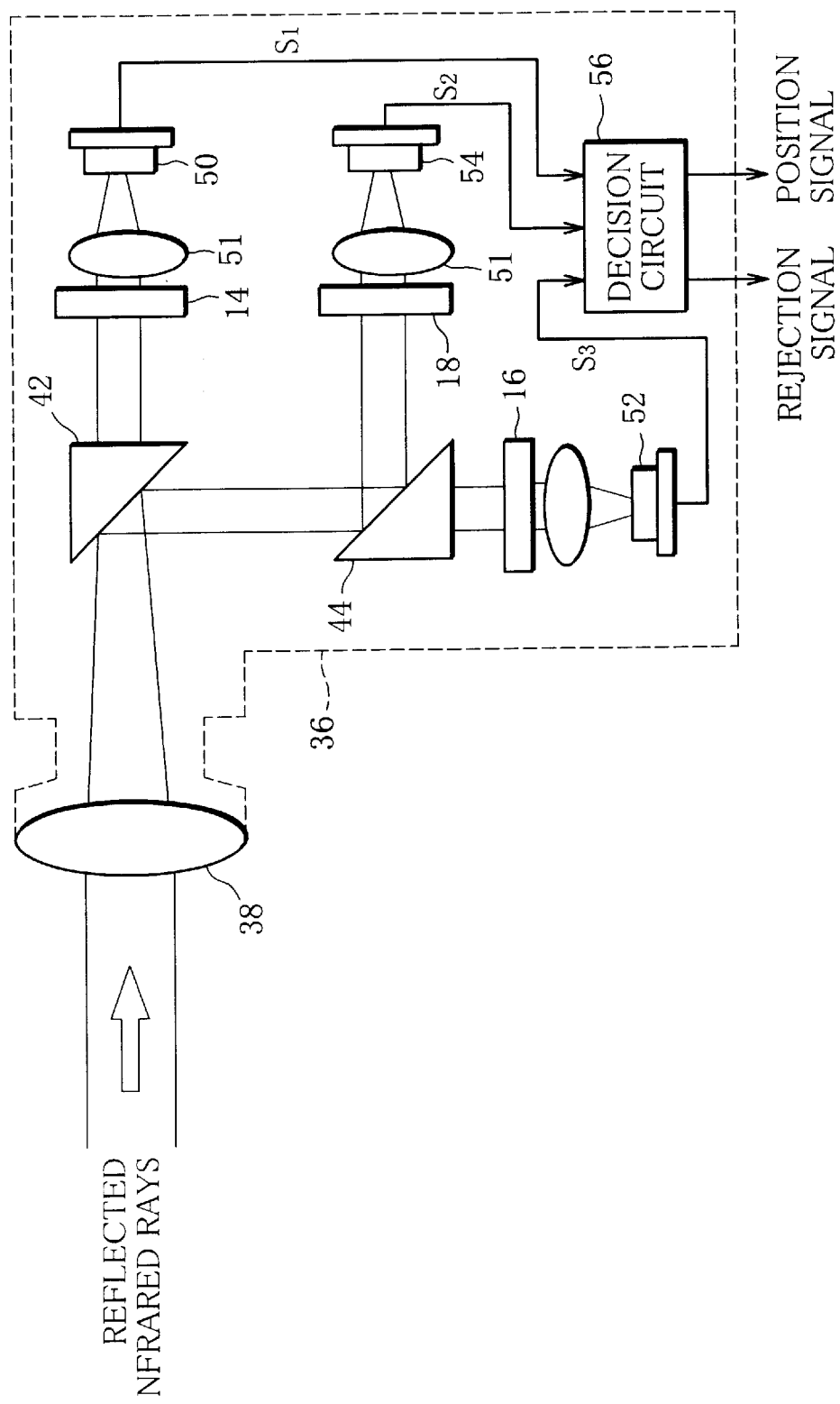
FIG. 5 is a schematic view showing a configuration of the infrared camera of FIG. 4.

Then, FIGS. 4 and 5 show a detecting apparatus and a detecting method of a second embodiment.

The detecting apparatus of the second embodiment comprises an infrared camera 36 over the conveyor 2. The infrared camera 36 has a range that covers the overall width of the conveyor 2, and its internal configuration is specifically shown in FIG. 5. The infrared camera 36 has a camera lens 38. The camera lens 38 converges the reflected infrared rays from the material T on the conveyor 2, and supplies the reflected infrared rays to a dichroic mirror 42.

The dichroic mirror 42 transmits and directs some of the reflected infrared rays from the camera lens 38 toward the first band-pass filter 14, and on the other hand, deflects the remainder toward a dichroic mirror 44. Further, the dichroic mirror 44 transmits and directs some of the reflected infrared rays from the dichroic mirror 42 toward the second band-pass filter 16, and on the other hand, deflects the remainder toward the third band-pass filter 18.

As mentioned before, the first to third band-pass filters 14 to 18 extract the first to third wavelength components, respectively, from the reflected infrared rays, and the extracted wavelength components are supplied to first to third infrared line scanners 50, 52 and 54 through condensing lenses 51, individually.

The first to third infrared line scanners 50, 52 and 54 include CCD arrays. The CCD arrays convert the respective reflection intensities of the wavelength components incident thereon into electrical signals, and output these electrical signals as the detection signals $S_1$, $S_2$, and $S_3$, individually. Each detection signal indicates the reflection intensity distribution of each corresponding infrared spectrum with respect to the transverse direction of the conveyor 2.

The detection signals from the individual infrared line scanners 50, 52 and 54 are supplied to a decision circuit 56 that has the same function as the aforesaid decision circuit 26. The decision circuit 56 detects the impurities in the material T, also determines the position of detection of the impurities with respect to the transverse direction of the conveyor 2, and outputs a position signal for the determined position. Thus, the detecting apparatus and the detecting method of the second embodiment, like the detecting apparatus and the detecting method of the first embodiment, can also accurately detect the various impurities in the material T.

Figure 6:
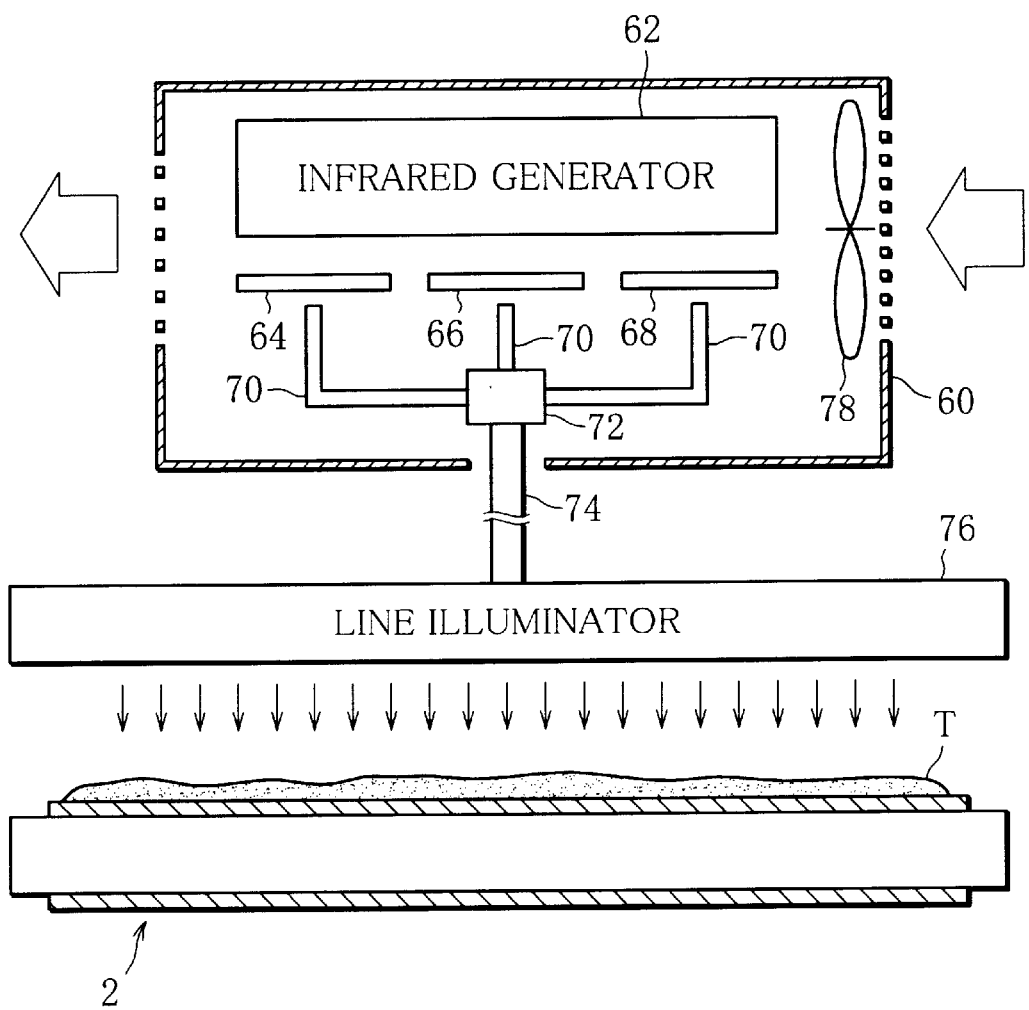
FIG. 6 is a view showing a part of a detecting apparatus of a third embodiment.
Figure 7:
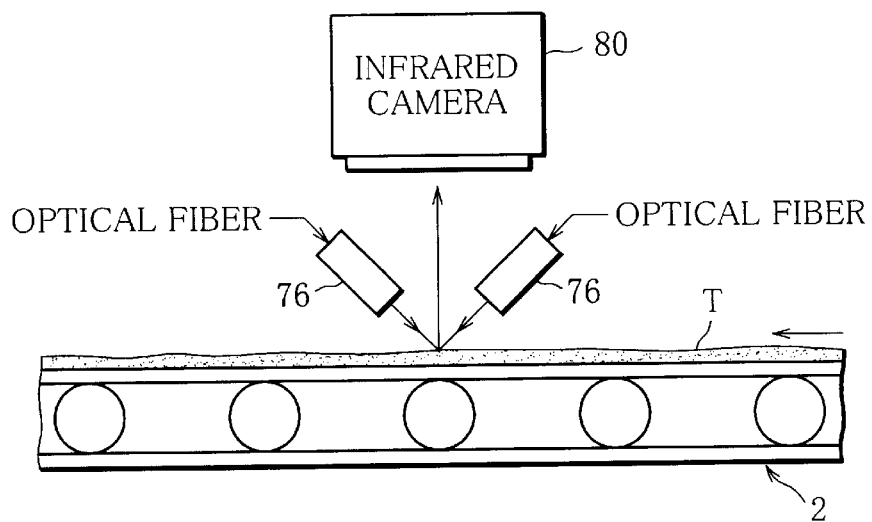
FIG. 7 is a view showing a line illuminator and an infrared camera used in the detecting apparatus of FIG. 6.
Figure 8:
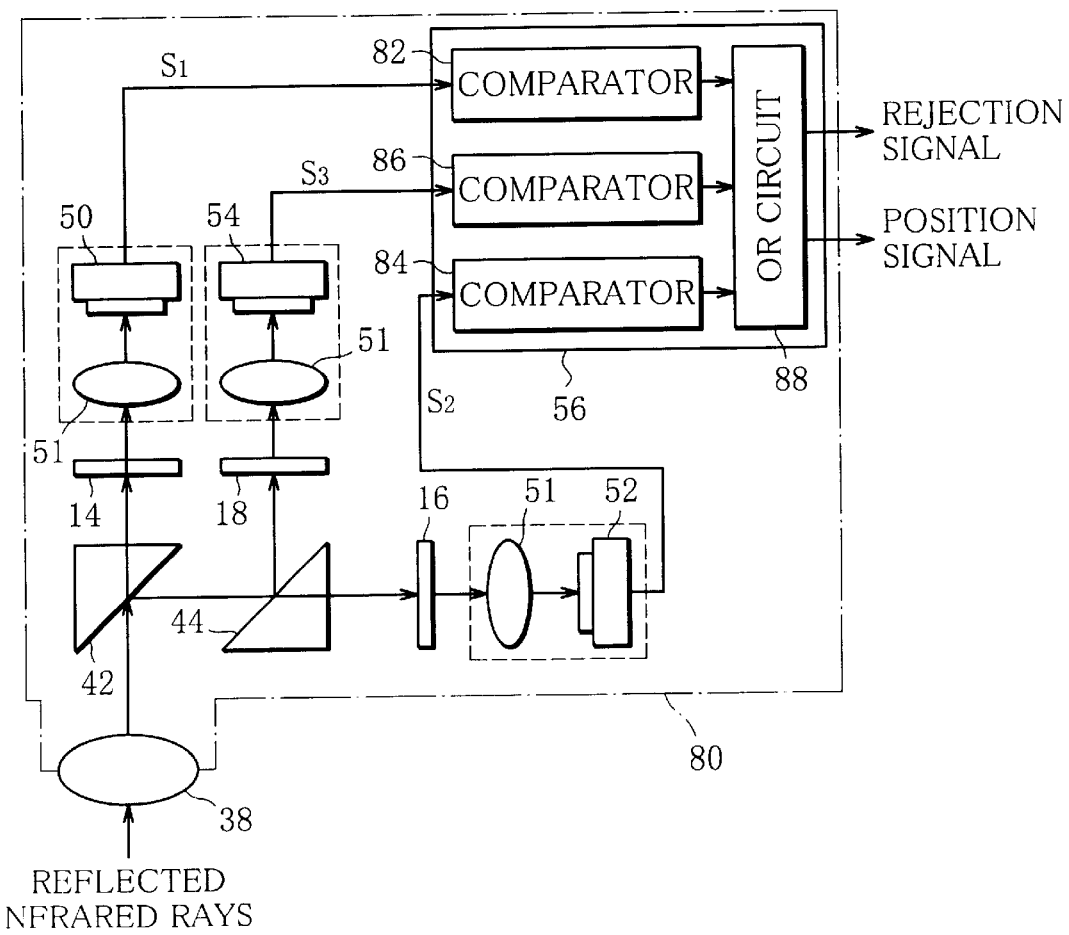
FIG. 8 is a view showing a configuration of the infrared camera of FIG. 7.

Then, FIGS. 6 to 8 show a detecting apparatus and a detecting method of a third embodiment.

The detecting apparatus of the third embodiment comprises a housing 60, and the housing 60 contains an infrared generator 62 therein. The infrared generator 62 may include, for example, a halogen lamp, sodium lamp, or infrared heater.

Infrared rays generated from the infrared generator 62 are transmitted through first to third band-pass filters 64, 66 and 68 and emitted toward their corresponding optical fibers 70, individually. The first to third band-pass filters 64, 66 and 68 can receive only the aforesaid first to third wavelength components of the infrared rays, and guide the received wavelength components to their corresponding optical fibers 70.

The optical fibers 70 are connected optically to a joint 72, and two optical fibers 74 extend from the joint 72. Thus, only the three specified wavelength components of the infrared rays generated from the infrared generator 62 are guided to the optical fibers 74. The optical fibers 74 extend from the housing 60 toward the conveyor 2 and are connected optically to line illuminators 76, individually.

The line illuminators 76, which are located over the conveyor 2, extend in the transverse direction of the conveyor 2 and are spaced in the running direction of the conveyor 2. Thus, the line illuminators 76 uniformly apply only the three wavelength components of the infrared rays to the material T on the conveyor 2, and the material T reflects the three wavelength components. Preferably, the two line illuminators 76 should share the same illumination line, as shown in FIG. 7.

Further, a cooling fan 78 is located in the housing 60. When the cooling fan 78 is rotated, the cooling fan 78 generates a current of the outside air that passes around the infrared generator 62 in the housing 60, and the outside air cools the infrared generator 62.

As shown in FIG. 7, an infrared camera 80 is located over the conveyor 2. The infrared camera 80 receives infrared rays reflected by the material T, that is, the first to third wavelength components of the infrared rays, and detects impurities in the material T and determines the position of the impurities in accordance with the respective reflection intensities of the first to third wavelength components.

As shown in FIG. 8, the infrared camera 80 has the same configuration as the aforesaid infrared camera 36. FIG. 8 shows a decision circuit 56 of the infrared camera 80 more specifically.

The decision circuit 56 includes first to third comparators 82, 84 and 86. These comparators receive detection signals S from their corresponding infrared line scanners and compare the received detection signals with their respective threshold values.

More specifically, the first comparator 82 has a first threshold value corresponding to a middle reflection intensity between those of the impurities B and the tobacco leaves $T_4$, with respect to the reflection intensity of the first wavelength component. That is, the middle reflection intensity is equivalent to the lower limit value of the aforesaid reflection intensity region $R_1$ (see FIG. 2),. If the first detection signal $S_1$ is smaller than the first threshold value, the comparator 82 delivers a rejection signal through an OR circuit 88. The rejection signal outputted in this case indicates that the detected impurities are B or C.

On the other hand, the second comparator 84 has a second threshold value of a level indicative of the tobacco leaves $T_1$, with respect to the reflection intensity of the second wavelength component. If the second detection signal $S_2$ is greater than the second threshold value, the second comparator 84 delivers a rejection signal through the OR circuit 88. The rejection signal outputted in this case indicates that the detected impurities are A.

Further, the third comparator 86 has a third threshold value of a level indicative of the tobacco leaves $T_4$, with respect to the reflection intensity of the third wavelength component. If the third detection signal $S_3$ is smaller than the third threshold value, the third comparator 86 delivers a rejection signal through the OR circuit 52. The rejection signal outputted in this case indicates that the detected impurities are B or C.

Thus, the detecting apparatus and the detecting method of the third embodiment, as in the cases of the first and second embodiments described above, can not only accurately detect various impurities in the material T, but also prevent thermal deterioration of the material T. More specifically, in the case of the third embodiment, only the first to third wavelength components of the infrared rays are applied to the material T, so that the material T cannot be overheated. Thus, there is no possibility of the tobacco leaves drying excessively or the flavor of the tobacco leaves worsening.

The detecting apparatus of the third embodiment may also comprise line illuminators that independently apply the first to third wavelength components of the infrared rays to the material T and infrared cameras paired with the individual line illuminators. The line illuminators are spaced from one another in the running direction of the conveyor. In this case, each infrared camera need not have a function to extract a specific wavelength component from the reflected infrared rays.

Figure 9:
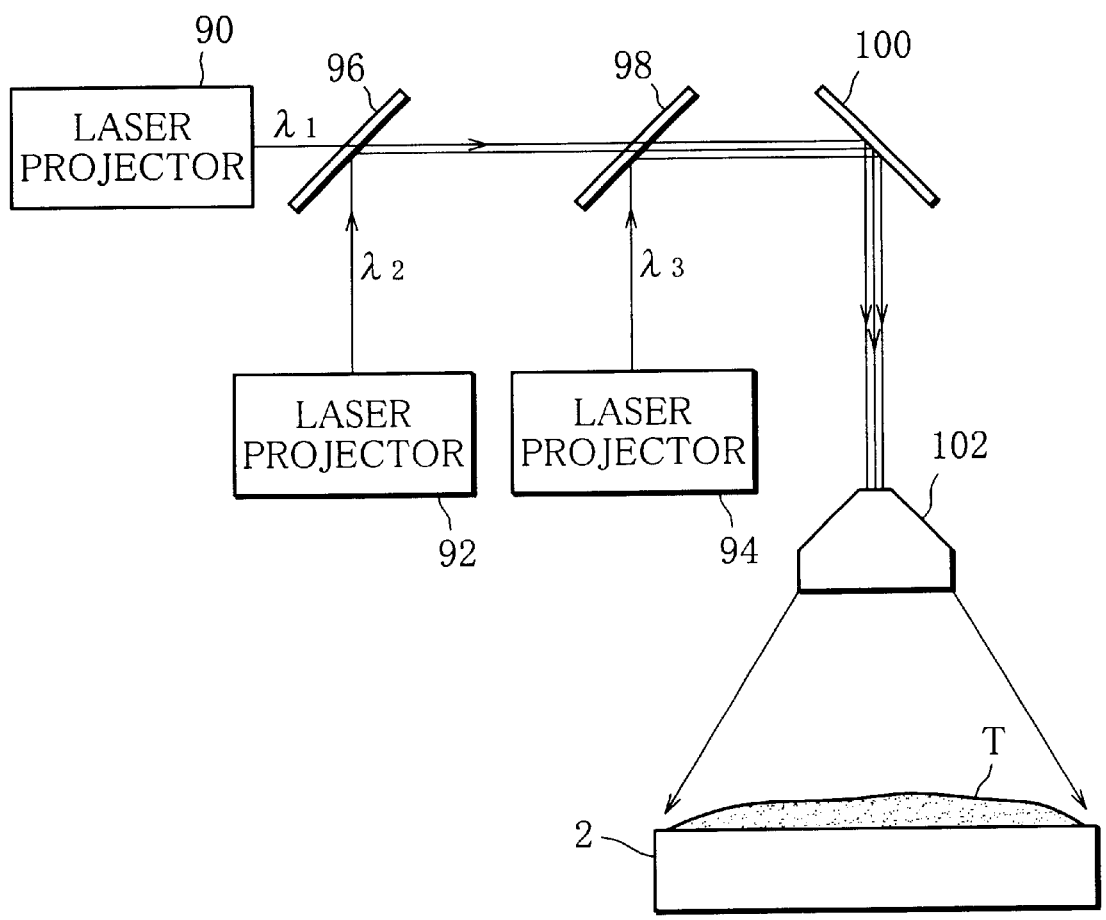
FIG. 9 is a view showing a part of a detecting apparatus of a fourth embodiment.

FIG. 9 shows a detecting apparatus and a detecting method of a fourth embodiment.

The detecting apparatus of the fourth embodiment comprises first to third laser projectors 90, 92 and 94. These laser projectors emit first to third laser beams $\lambda_1$, $\lambda_2$, and $\lambda_3$ of different wavelengths, respectively. The first laser beam $\lambda_1$, from the first laser projector 90 is reflected onto a laser line generator 102 by a total-reflection mirror 100 after it passes through half-mirrors 96 and 98. The laser line generator 102 applies the first laser beam $\lambda_1$, to the material T on the conveyor 2.

The first and second laser beams $\lambda_2$ and $\lambda_3$ from the second and third laser projectors 92 and 94 are reflected by their corresponding half-mirrors and the total-reflection mirror 100, and applied, along with the first laser beam $\lambda_1$, to the material T on the conveyor 2.

It is to be understood that the first to third laser beams $\lambda_1$, $\lambda_2$, and $\lambda_3$, like the aforesaid first to third wavelength components of the infrared rays, are selected among wavelengths that produce definite differences in reflection intensity between the material T and various impurities. In the case of the detecting apparatus of the fourth embodiment also, the impurities in the material T are detected in accordance with the respective reflection intensities of the laser beams by the same method as the decision methods of the second and third embodiments.

The detecting apparatus of the fourth embodiment may use a light transmission path composed of the optical fibers 14 and 18 in place of the mirrors and lenses.

In any of the embodiments described above, the impurities in the material T are detected in accordance with the three wavelength components of the light reflected by the material T. However, the impurities can be detected by using only two wavelength components. More specifically, the impurities A, B, and C can be detected in accordance with the first and second detection signals $S_1$, and $S_2$ only or the second and third detection signals $S_2$ and $S_3$ only, as seen from FIG. 2.

The wavelength components of the infrared rays used in the detection of the impurities are not limited to the aforesaid wavelengths, 1,200 nm, 1,700 nm, and 1,940 nm, and any wavelength components may be used only if they produce definite differences in reflection intensity between the material and the impurities.

In the case where the material contains any other impurities than A to C, moreover, wavelength components suited for the detection of these impurities are used.

The detecting apparatus and the detecting method of the present invention are applicable to various materials such as single-variety tobacco leaves, cut tobacco obtained by cutting tobacco leaves, etc.

What is claimed is:

1. A detecting apparatus for detecting a plurality of kinds of impurities in a material consisting of tobacco leaves, said detecting apparatus comprising:

an illuminating device for applying detection light to the material when the material is transported;

a plurality of light receiving devices for receiving the detection light reflected by the material and outputting respective reflection intensities of a plurality of wavelength components of said detection light, where the specific wavelength components have different reflection intensities, respectively, between the material and said plurality of kinds of impurities; and a decision circuit for comparing the reflection intensities of said specific wavelength components that are output by said light receiving device with reference reflection intensities of said specific wavelength components that are inherent in the material, and detecting said plurality of kinds of impurities in the material on the basis of the result of the comparison, the decision circuit having a first gate circuit, a second gate circuit, and a third gate circuit, each of which has a different upper and a different lower threshold value, and each of which is connected to an OR circuit.

2. The apparatus according to claim 1, wherein said illuminating device includes a source of generation for generating infrared rays as said detection light, and each of said plurality of light receiving devices includes extracting means for extracting said specific wavelength components of the infrared rays reflected by the material.

3. The apparatus according to claim 2, wherein said illuminating device further includes a rotatable polygon mirror, said polygon mirror being capable of reflecting the infrared rays from said source of generation onto the material on the conveyor and scanning the material on the conveyor with said reflected infrared rays in the transverse direction of the conveyor.

4. The apparatus according to claim 3, wherein said polygon mirror transmits said reflected infrared rays from the material to said light receiving device.

5. The apparatus according to claim 1, wherein said illuminating device applies only said specific wavelength components of said detection light to the material.

6. The apparatus according to claim 5, wherein said illuminating device includes a source of generation for generating infrared rays as said detection light and extracting means for extracting said specific wavelength components from said source of generation, and only said extracted specific wavelength components are applied to the material on the conveyor.

7. The apparatus according to claim 6, wherein said illuminating device further includes cooling means for cooling said source of generation.

8. A detecting method for detecting a plurality of kinds of impurities in a material consisting of tobacco leaves, said detecting method comprising:

applying detection light to the material when the material in transported;

receiving the detection light reflected by the material and outputting respective reflection intensities of a plurality of wavelength components of said detection light, where said plurality of wavelength components have different reflection intensities, respectively, between the material and said plurality of kinds of impurities; and comparing the output reflection intensities of said specific wavelength components with reference reflection intensities of said specific wavelength components that are inherent in the material, and detecting said plurality of kinds of impurities in the material on the basis of the result of the comparison, the decision circuit having a first gate circuit, a second gate circuit, and a third gate circuit, each of which has a different upper and a different lower threshold value, and each of which is connected to an OR circuit.

9. The method according to claim 8, wherein said detection light is infrared rays, and said specific wavelength components of the infrared rays reflected by the material are extracted.

10. The method according to claim 8, wherein said detection signal is infrared rays composed of said specific wavelength components only.

11. The method according to claims 8, wherein in the step of outputting respective reflection intensities of said specific wavelength components, respective reflection intensities of at least three specific wavelength components are output.

12. The apparatus according to claim 1, wherein said light receiving device outputs respective reflection intensities of at least three specific wavelength components of said detection light.

13. The apparatus according to claim 1, wherein said light receiving device includes an infrared camera having a range that covers an entire transportation width of the material and being capable of receiving infrared rays reflected by the material, and said infrared camera includes:
dividing means for dividing the received reflected infrared rays into a plurality of separate beams of infrared rays,
a plurality of band-pass filters for extracting said specific wavelength components from said separate beams, respectively, said specific wavelength components differing from each other, and
a plurality of infrared line scanners for receiving said specific wavelength components extracted by said band-pass filters and outputting reflection intensity distributions of the received specific wavelength components, respectively.

* * * * *

UNITED STATES PATENT AND TRADEMARK OFFICE
CERTIFICATE OF CORRECTION

PATENT NO. : 6,614,531 B2
DATED : September 2, 2003
INVENTOR(S) : Kiyomi Sato et al.

It is certified that error appears in the above-identified patent and that said Letters Patent is hereby corrected as shown below:

<u>Title page,</u>
Item [30], Foreign Application Priority Data please insert:
-- [30] Foreign Application Priority Data
June 8, 1999 (JP).............................................. 11-161017

March 24, 2000 (JP)......................................... 2000-084542 --

Signed and Sealed this

Fourth Day of May, 2004

JON W. DUDAS
*Acting Director of the United States Patent and Trademark Office*